United States Patent [19]

Nathanson

[11] Patent Number: 4,892,871

[45] Date of Patent: Jan. 9, 1990

[54] AZIDO-SUBSTITUTED OCTOPAMINE AGONISTS AND THE USE THEREOF TO CONTROL INVERTEBRATE PESTS

[75] Inventor: James A. Nathanson, Wellesley, Mass.

[73] Assignee: The General Hospital Corporation, Boston, Mass.

[21] Appl. No.: 180,758

[22] Filed: Apr. 12, 1988

[51] Int. Cl.$^4$ .................... A01N 43/86; A01N 43/50; C07D 233/50
[52] U.S. Cl. .................. 514/227.2; 514/228.8; 514/275; 514/329; 514/370; 514/377; 514/392; 514/426; 544/53; 544/54; 544/88; 544/330; 544/332; 546/223; 548/190; 548/193; 548/194; 548/198; 548/234; 548/315; 548/559
[58] Field of Search .............. 548/315, 234, 193, 194, 548/198, 190, 559; 544/330, 332, 88, 53, 54; 546/223; 514/39.2, 275, 377, 228.8, 370, 227.2, 426, 329

[56] References Cited

U.S. PATENT DOCUMENTS

| | | | |
|---|---|---|---|
| 3,867,448 | 2/1975 | Duerr et al. | 564/245 |
| 3,960,947 | 6/1976 | Duerr et al. | 564/220 |
| 4,020,066 | 4/1977 | Bosshard et al. | 544/198 |
| 4,020,067 | 4/1977 | Bosshard et al. | 544/198 |
| 4,277,493 | 7/1981 | Sinharay et al. | 514/522 |
| 4,678,775 | 7/1987 | Nathanson | 514/47 |

OTHER PUBLICATIONS

*Chemical Abstracts,* 104:289182 (1986) [Kawamara, R., et al., *Eur. J. Pharmacol.,* 1985, 117(1), 43-50].
Nathanson, J. A., *Mol. Pharm.* 28: 254-268 (1985).
Nathanson, J. A., *Proc. natl. Acad. Sci. (U.S.A.)* 82: 599-603 (1985).
Hollingworth, R. M., *Environ. Health Persp.* 14: 57-69 (1976).
De Jong, A. P. et al., *Eur. J. Pharm.* 69: 175-188 (1981).
Matsumura, F. et al., *Environ. Health Persp.* 14: 71-82 (1976).

*Primary Examiner*—Richard A. Schwartz
*Attorney, Agent, or Firm*—Saidman, Sterne, Kessler & Goldstein

[57] ABSTRACT

The invention is directed to azido-substituted octopamine agonists and the radiolabeled derivatives thereof. The invention also relates to past controlling compositions comprising the azido-substituted octopamine agonists of the invention.

The invention also relates to methods of controlling invertebrate pests by bringing the pest into contact with an invertebrate pest-controlling composition of the invention and to an apparatus for controlling invertebrate pests utilizing the pest-controlling compositions of the invention. The pest-controlling compositions may be used alone or in conjunction with ultraviolet light.

The invention also relates to methods for the isolation of octopamine receptor proteins utilizing the radiolabeled azido-substituted octopamine agonists of the invention.

14 Claims, 8 Drawing Sheets

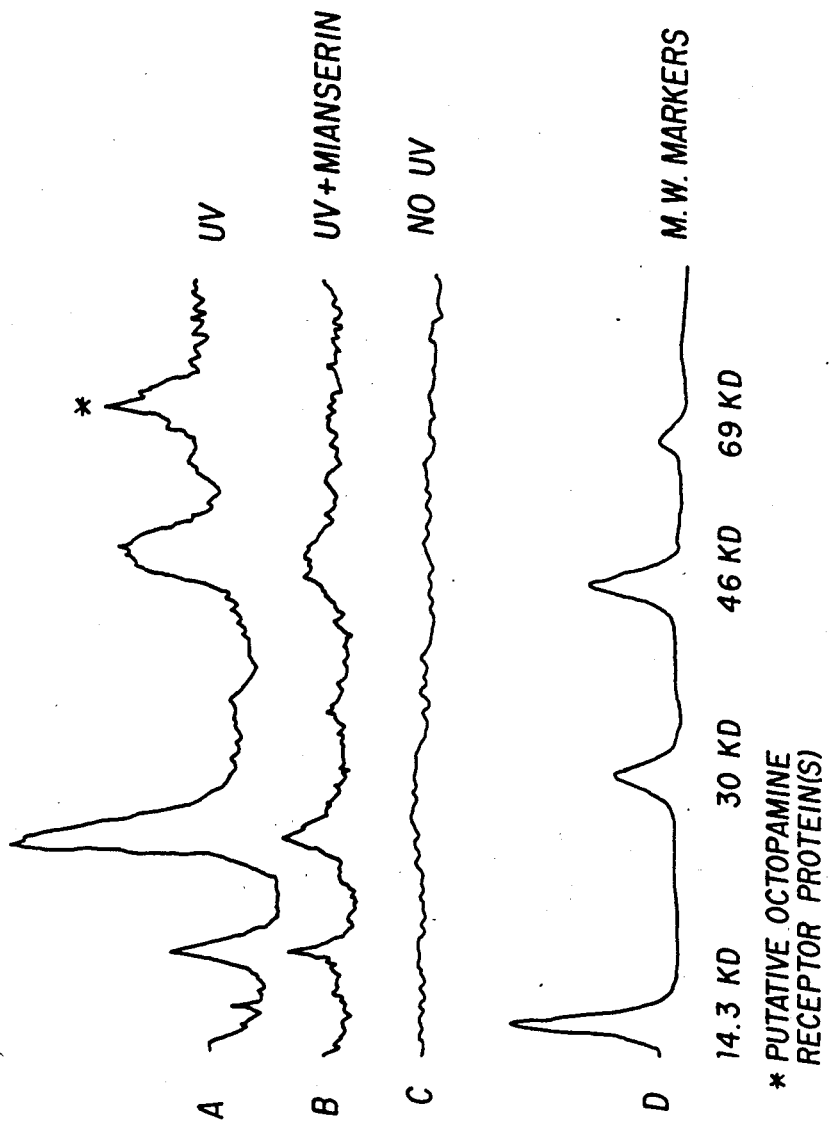

AZIDO-SUBSTITUTED OCTOPAMINE AGONISTS AND THE USE THEREOF TO CONTROL INVERTEBRATE PESTS

BACKGROUND OF THE INVENTION

1. Field of the Invention

The present invention relates to azido-substituted octopamine agonists, and the radio-labeled derivatives thereof, having pest controlling activity and to methods of controlling pests by treatment with the aforementioned octopamine agonists. The invention also relates to an apparatus comprising a support structure, the azido-substituted octopamine agonists of the invention, and a UV light source. The invention also relates to methods for the isolation of octopamine receptor proteins utilizing the radiolabeled azido-substituted octopamine agonists of the invention.

2. Description of the Background Art

Despite the recent development and great promise of such advanced pest controlling compositions as chemical sterilants, pheromones or ecologically-based insect control strategies, it is doubtless that, at present, the use of chemical pesticides still plays a predominant role. The use of insecticides often represents the difference between profitable crop production for farmers and no marketable crop at all. The value of insecticides in controlling human and animal diseases has been dramatic.

Therefore, in parallel to the aforementioned newer technologies for pest control, there has been active research and investigation into the detailed biochemical modes of action of chemical pesticides. Thus, for example, Nathanson et al., *Molecular Pharmacology* 20:68-75 (1981) presented evidence indicating that the formamidine pesticides chlordimeform (CDM) and N-demethylchlordimeform (DCDM) may affect octopaminergic neurotransmission. CDM and DCDM have been reported to mimic the effects of octopamine in stimulating light emission in the firefly lantern (Hollingworth, R. M. et al., *Science* 208:74-76 (1980)), and in effecting nerve-evoked muscle responses in the locust leg (Evans, P. D., *Nature* 287:60-62 (1980)). Nathanson et al., supra, found that DCDM, the probable in vivo metabolite of CDM, is about six-fold more potent than octopamine itself as a partial agonist of adenylate cyclase stimulation. Stimulation by the formamidines results in increased formation of the intracellular messenger, cyclic AMP. This stimulation was blocked by cyproheptadine, clozapine, fluphenazine and phentolamine compounds, also known to block the octopamine receptor. Nathanson et al. concluded that DCDM is the most potent octopaminergic compound described.

Similar results were observed by Hollingworth et al. (reported in the Scientific Papers of the Institute of Organic and Physical Chemistry of Wroclaw Technical University, No. 22, Conference 7 (1980)). These authors demonstrated that certain formamidines act on octopamine receptors to induce the synthesis of cyclic AMP, and that this response is blocked by both phentolamine and cyproheptadine, which are known to act as octopaminergic antagonists in insects. The authors also suggested that these formamidines are potent simulators of the octopamine sensitive adenylate cyclases in the thoracic ganglia of *Periplaneta americana*, and in the ventral nerve cord and fat body of *M. sexta*. The authors suggest that the stimulation of octopamine receptors underlies a number of toxic responses seen with formamidines on insects.

However, use of formamidines as pest controlling agents gives rise to certain problems, including the fact that the aniline breakdown products are carcinogenic. Moreover, a further problem is that the range of activity of these compounds is limited to a relatively few insect species. Matsumura, F., et al.. *Environ. Health Perspect.* 14: 71-82 (1976). Applicant has observed that didemethylchlordimeform (DDCDM) is a full agonist, 20-fold more potent than octopamine in Manduca. but only a very weak and partial agonist in the cockroach. Consistent with this in vitro activity, the formamidines are toxic in Manduca but not in the cockroach.

It should be noted that the presence of an insect adenylate cyclase enzyme which is sensitive to naturally occurring D(−) octopamine as a "neurotransmitter" has been known for some time (Nathanson et al., *Science* 180:308-310 (1973) (cockroach); Nathanson, ibid. 203:65-68 (1979) (firefly); Evans, J., *Neurochem.* 30:1015-1022 (1978) (cockroach)).

The study of cyclic AMP (cAMP) as a "second messenger" has led to the accepted model that a hormone or neurotransmitter binds at a cell-membrane bound receptor, which activates adenylate cyclase to a form capable of converting ATP in the cytoplasm of the cell into cAMP. cAMP then relays the signal brought by the hormone or neurotransmitter from the membrane to the interior of the cell. Agonists of the hormone or neurotransmitter are, by definition, capable of eliciting the same response (see, for example, Nathanson and Greengard, *Scientific American* 237:108-119 (1977)). Once formed inside the cell, cAMP presumably binds to a protein kinase which is then capable of phosphorylating appropriate proteins, etc.

Recently, a class of octopamine receptor agonists comprising substituted phenyliminoimidazolidines have been described. These compounds show antifeeding activity in *Manduca sexta* and interact with octopamine receptors which are distinct from mammalian adrenergic (including alpha-1, alpha-2, beta-1, beta-2), dopaminergic, $5HT_1$, and $5HT_2$ receptors. Nathanson, J. A. in "Abstr. 2nd Internatl. Sym. Insect Neurobiol. Pest Action," Society of Chemical Industry, London (1985); Nathanson, J. A., *Proc. Natl. Acad. Sci. (USA)* 82:599-603 (1985); and Nathanson, J. A., *Mol. Pharmacol.* 28:254-268 (1985).

In order to allow development of further octopamine agonists which are effective against a wide variety of insect species and which In order to allow development of further octopamine agonists which are effective against a wide variety of insect species and which have a wide spectrum of pesticidal activity, a need exists for additional information about the molecular pharmacology of octopamine receptors and the interspecies differences in the characteristics of these receptors.

SUMMARY OF THE INVENTION

The present invention arose out of the initial observations by the inventor and others that the mode of action of certain formamidine and non-formamidine pesticides was through their octopaminergic agonist activity on octopamine receptors present in the pest, and that these pest control agents were acting through generation of cAMP as a "second messenger." It was not clear at the time of these observations whether these were generalizable observations or were isolated instances. The inventor has now observed that azido-substituted octopaminergic agonists are also pest control agents. Thus, the present invention provides a pest controlling composition which comprises an azido-substituted octopamine agonist toward an octopamine receptor present in said pest having the formula (I):

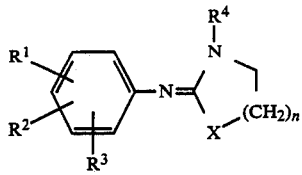

wherein
R$^1$ is azido,
R$^2$ and R$^3$ are the same or different and selected from the group consisting of hydrogen, azido, hydroxy, fluorine, bromine, chlorine, iodine, nitro, lower (C$_1$-C$_6$) alkyl, lower (C$_1$-C$_6$) alkoxy, lower haloalkyl, amino, mono-lower alkyl amino, di-lower alkyl amino, hydroxy substituted alkyl amino, lower acyl amino, and R$^2$ and R$^3$ may together form a fused ring;
R$^4$ is hydrogen, lower alkyl or lower alkyl substituted by hydroxy or lower alkoxy;
n=1 or 2; and
X is N, O, CH$_2$, or S.

The invention also relates to azido-substituted formamidines of the formula (IX):

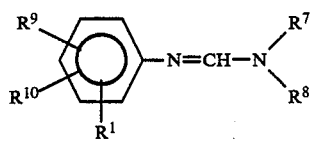

wherein
R$^1$ is azido,
R$^7$ and R$^8$ are hydrogen, C$_1$-C$_6$ alkyl or C$_1$-C$_6$ alkyl substituted by hydroxy or C$_1$-C$_6$ alkoxy;
R$^9$ and R$^{10}$ are the same or different and selected from the group consisting of hydrogen, azido, hydroxy, fluorine, chlorine, bromine, iodine, nitro, C$_1$-C$_6$ alkyl, C$_1$-C$_6$ alkoxy, C$_1$-C$_6$ haloalkyl, amino, mono C$_1$-C$_6$ alkyl amino, di- C$_1$-C$_6$ alkylamine, C$_1$-C$_6$ alkyl substituted by hydroxy, and C$_2$-C$_6$ acyl amino.

The invention also relates to azido-substituted phenylethylamines having the formula (X):

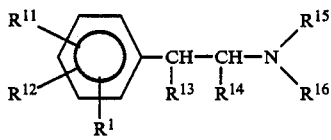

wherein
R$^1$ is azido,
R$^{11}$ and R$^{12}$ are the same or different and selected from the group consisting of hydrogen, azido, hydroxy, fluorine, chlorine, bromine, iodine, nitro, C$_1$-C$_6$ alkyl, C$_1$-C$_6$ alkylamine, C$_1$-C$_6$ alkyl substituted by hydroxy, and C$_2$-C$_6$ acyl amino; and
R$^{13}$, R$^{14}$, R$^{15}$ and R$^{16}$ are the same or different and selected from the group consisting of hydrogen, C$_1$-C$_6$ alkyl, C$_1$-C$_6$ alkyl substituted by hydroxy or C$_1$-C$_6$ alkoxy.

The invention also relates to azido-substituted 2-benzylimidazolines of the formula (XI):

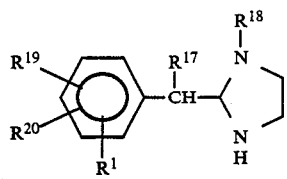

wherein
R$^1$ is azido,
R$^{18}$ is selected from the group consisting of hydrogen, C$_1$-C$_6$ alkyl and C$_1$-C$_6$ alkyl substituted by hydroxy or C$_1$-C$_6$ alkoxy; and
R$^{17}$, R$^{19}$ and R$^{20}$ are the same or different and selected from the group consisting of hydrogen, azido, hydroxy, fluorine, chlorine, bromine, iodine, nitro, C$_1$-C$_6$ alkyl, C$_1$-C$_6$ alkoxy, C$_1$-C$_6$ haloalkyl, amino, mono- C$_1$-C$_6$ alkylamino, di- C$_1$-C$_6$ alkylamino, C$_1$-C$_6$ alkyl substituted by hydroxy, and C$_2$-C$_6$ acylamino.

The invention also relates to radiolabeled derivatives of the azido-substituted octopamine agonists of the invention and the use thereof for the isolation and characterization of octopamine receptors.

The invention also relates to an apparatus for the control of invertebrate pests comprising:

(a) a support structure having first and second locations;

(b) the azido-substituted octopamine agonist of the invention together with a pesticidally inert carrier or bait disposed at said first location for contact by an invertebrate pest; and (c) a UV light source, disposed at said second location, wherein said source is in optical communication with said invertebrate pest after said invertebrate pest has contacted said agonist, whereby the pesticidal effectiveness of said agonist is enhanced.

In response to the need for probes that allow the isolation and biochemical characterization of octopamine receptor proteins, the radiolabeled azido-substituted octopamine agonists of the invention have been developed. The azido-substituted compounds display the property, when photoactivated by ultraviolet light, of binding irreversibly to octopamine receptors.

The octopamine agonists of the invention are highly selective pest control agents since vertebrate species—as opposed to invertebrate, e.g., insect, species—lack octopamine receptors. In addition, these octopamine agonists are highly active and unexpectedly have activities greater than one hundred times higher than octopamine. Octopamine agonists act by binding to a receptor which activates adenylate cyclase which, in turn, produces secondary messenger cyclic AMP. The cyclic AMP acts by binding to a cyclic AMP receptor generating hormonal-type activity.

In another embodiment of the invention, there is provided a method for controlling pests by treating said pests with an octopamine agonist of the invention in an amount effective to provide pest control, by either pesticidal or pestistatic activity.

More specifically, the invention is directed to a method for controlling invertebrate pests comprising:

(a) bringing said pest into contact with an azido-substituted octopamine agonist of the invention in an amount sufficient to effect control of said pest when exposed to a UV light source, for a time sufficient to allow said agonist to complex with the octopamine receptors of said pest, and (b) exposing said pest to UV light, thereby causing the formation of an agonist-receptor conjugate and irreversibly activating adenylate cyclase to enhance the pest-controlling properties of the azido-substituted octopamine agonist.

DESCRIPTION OF THE FIGURES

FIG. 13 depicts densitometry scans of autoradiograms of receptor proteins labeled with VIII and separated on an SDS-polyacrylamide gel (lane A). In lane B, the receptor proteins were incubated in the presence of VIII and mianserin. In lane C, the sample was not irradiated with UV light. Lane D depicts the position of M.W. markers.

DESCRIPTION OF THE PREFERRED EMBODIMENTS

Figure 1:
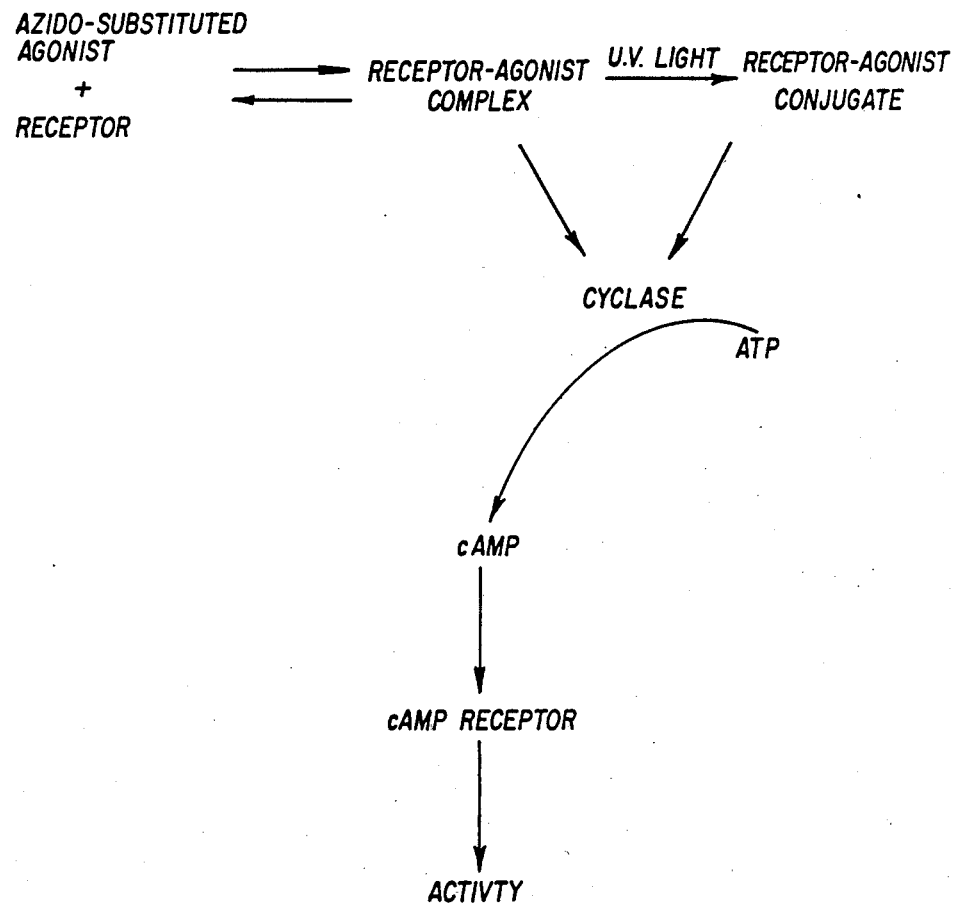
FIG. 1 depicts the mode of action of the compounds of the invention.

The azido-substituted octopamine agonists of the invention exhibit their pest-controlling activity by binding with octopamine receptors in an invertebrate pest and, thereby, activating adenylate cyclase. The mechanism of action for these octopamine agonists is depicted in FIG. 1. The binding of the azido-substituted octopamine agonists of the invention is normally reversible. However, when the azido-agonist-receptor complex is exposed to ultraviolet light, photolysis of the azido group occurs together with irreversible binding of the agonist to the octopamine receptor. This in turn causes an irreversible activation of adenylate cyclase which enhances the pest-controlling properties of the compounds of the invention.

The invention also relates to methods of controlling pests involving administering the pest-controlling composition of the invention to an invertebrate pest in conjunction with irradiation of the pest with ultraviolet light of sufficient strength and proper wavelength to penetrate the exoskeleton of the pest. The ultraviolet light may be provided by sunlight or by artificial means. The wavelength necessary to photolyze the azido group and thereby cause irreversible binding to the octopamine receptor is 210 to 310 nm. One of ordinary skill in the art can determine the intensity of ultraviolet light necessary to penetrate the exoskeleton of an invertebrate pest without undue experimentation.

Also included within the scope of the invention is an apparatus for controlling invertebrate pests comprising:

(a) a support structure having first, second and third locations;

(b) an azido-substituted octopamine agonist of the invention together with a pesticidally inert carrier or bait disposed at said first location for contact by an invertebrate pest; and (c) a UV light source, disposed at said second location, wherein said source is in optical communication with said invertebrate pest at said third location, wherein said third location is adjacent to said first and second locations whereby the pesticidal effectiveness of said agonist is enhanced.

The apparatus may further comprise a partially closed housing with apertures to allow the pests to enter or exit and which contains an azido-substituted agonist of the invention and a UV light source. The support structure serves to fix the UV light so that the pest is in optical communication with UV light after contacting the agonist. The housing may be configured to prevent the UV light from emanating from said housing. The agonist and UV light source may also be configured so they are not in direct optical communication. This configuration prevents premature photolysis of the azido group before the agonist has contacted an invertebrate pest.

The apparatus may further comprise means for delaying the passage of the pest from the first location, wherein the azido-substituted agonists is disposed, to the third location wherein the UV light source is in optical communication with the pest. Such means may comprise, for example, a system of baffles which prolong the length of time necessary to traverse the distance between the first and third locations. By providing for decay in traversing the distance between the first and third locations, the effectiveness of the azido-substituted octopamine agonist is further enhanced by providing a time sufficient for the agonist to complex with the octopamine receptor of the pest before exposure to the UV light source. One of ordinary skill in the art can determine the time delay necessary to give optimum effectiveness of the azido-substituted octopamine agonist without undue experimentation.

In this embodiment, the housing may comprise apertures through which pests may enter the first location. Such apertures may be configured to allow entry of the pest, but retard egress of the pest. For example, the apertures may comprise truncated cones rigidly affixed and pointing into the housing section which surrounds the first location of the support structure. The larger end of the truncated cone is affixed to the housing at a location wherein a hole of the same diameter as the larger end of the cone is located. The larger diameter is selected to allow easy entry by the pest. The smaller diameter is selected to be just large enough to allow entry by the pest, but to inhibit egress. The larger and smaller diameters may be selected by one of ordinary skill in the art without undue experimentation. The length of the truncated cone is not critical, but will be of sufficient length to achieve the intended purpose. The length of the truncated cone may also be determined by one of skill in the art without undue experimentation.

The terms "pest controlling" or "pest controlling activity," used throughout the specification and claims, are meant to include any pesticidal (killing) or pestistatic (preventing the host plant from being eaten, or inhibiting, maiming or generally interfering) activities of a composition against a given pest at any stage in its lie cycle. Thus, these terms not only include killing, but also include the production of behavioral abnormalities (e.g., tremor, incoordination, hyperactivity, anorexia, leaf walk-off behavior) which interfere with activities such as, but not limited to, eating, molting, hatching, mobility or plant attachment. The terms also include chemosterilant activity which produces sterility in insects by preventing the production of ova or sperm, by causing death of sperm or ova, or by producing severe injury to the genetic material of sperm or ova, so that the larvae that are produced do not develop into mature progeny.

The terms also include repellant activity that protect animals, plants or products from insect attack by making food or living conditions unattractive or offensive. These repellant activities may be the result of repellants which may be poisonous, mildly toxic, or non-poisonous.

The terms also include activities as attractants, food lures, sex pheromones, aggregation pheromones, and the like. Any compound which has a "pest controlling activity" of greater than $K_a^{oct}/K_a^{(Azido)} = 1$, as determined in the broken cell preparations of the firefly light organ as described more fully below, is included in the present invention.

By the terms "radiolabeled derivative" is intended the octopamine agonists of the invention wherein one or more of the atoms thereof are enriched in a radioisotope or wherein the octopamine agonist is covalently coupled to a radioisotope label. Examples of such radioactive isotopes which may enrich the octopamine agonist include, but are not limited to $^3H$ and $^{14}C$. Examples of radioisotopes which may be used to covalently label the molecule include $^{125}I$, $^{131}I$, $^{32}P$, $^{35}S$, $^{51}Cr$, $^{36}Cl$, $^{57}Co$, $^{58}Co$, $^{59}Fe$ and $^{75}Se$.

The question of whether a given azido-substituted compound within the scope of the invention is an octopamine agonist can be readily answered by measuring adenylate cyclase activity of the octopamine-sensitive adenylate cyclase present in broken cell preparations of the firefly light organ. Generally, the broken cell preparations are prepared according to the method described by Nathanson et al. (*Molecular Pharmacology* 20:68-75 (1981)), which is herein incorporated by reference. Specimens of *Photinus pyralis* are prepared by opening their tail sections, cleaning them, removing the light organs, and homogenizing the cyclase-containing fraction. Adenylate cyclase activity is measured in appropriate buffer-containing ATP, cofactors, and the compound to be tested. Normally, the solution mixture contains a phosphodiesterase inhibitor such as theophylline, and the assay is designed to provide linear measurements with respect to time and enzyme concentration. If necessary, the compounds to be tested are initially solubilized and appropriate solvent controls are run in parallel. The enzyme reaction is initiated by addition of ATP, stopped by heating, and centrifuged. Cyclic AMP can be measured by any test which indicates the presence thereof, preferably by the protein binding assay of Brown et al. (*Advances in Cyclic Nucleotide Research* 2:25-40 (1972)). The determination of the constant $K_a$, which is the concentration of the azido-substituted agonist necessary for half-maximal activation of cyclase activity, is carried out by measuring cyclase activity in the preparation, and plotting the activity (above control activity) versus the semilogarithm of the particular agonist concentration. This is done for a series of increasing concentrations until maximal activity (Vmax) is reached. $K_a^{(Azido)}$ is then calculated from the graph as the agonist concentration required for one-half of Vmax. $K_a^{(Azido)}$ is compared with the constant ($K_a^{oct}$) determined in an analogous way using ±p-octopamine as the agonist. The ratio $K_a^{oct}/k_a^{(Azido)}$ is then an indication of whether a particular azido-substituted agonist (Azido) is more (ratio greater than 1) or less (ratio smaller than 1) active than (±)-p-octopamine (oct). Maximal activation of enzyme activity as a percentage of maximal activation seen in the presence of (±) p-octopamine can be denoted as % Vmax. (Although the naturally occurring insect neurotransmitter is (−)-p-octopamine, the definition of an "agonist" in the present application is based on (±)-p-octopamine as the standard. Since an "agonist" is a compound that mimics the effect of (−)-p-octopamine, (−)-p-octopamine itself, free of substantial amounts of the (+) enantioner is not included in the definition).

Generally, an octopamine agonist having a $K_a^{oct}/K_a^{(Azido)}$ ratio greater than 1, preferably greater than 10, most preferably greater than 100, as measured by the firefly lantern test using a broken cell preparation, is used. Also, generally, octopamine agonists having Vmax anywhere between 5 and upwards of 100%, preferably between 10 and upwards of 100%, of the Vmax of (±)-p-octopamine can be used. The values of Vmax for any desired octopamine agonist are not as important as the values of the ratio of $K_a$'s. As long as the $K_a^{oct}/K_a^{(Azido)}$ ratio falls within the stated range, the Vmax values can vary widely.

In addition to the above method employing the firefly light organ, octopamine-sensitive adenylate cyclase can also be measured in tissue preparations from the nerve cord of any desired particular insect pest, using a modification of the method appearing in Nathanson et al., Science 180:308:310 (1973), herein incorporated by reference. In this modification (which is not necessary if the firefly light organ is used), dopamine (10 micromolar) and serotonin (10 micromolar) are added to all (including control) assay tubes. This is done in order to be sure that the tested compounds (I) are affecting only octopamine receptors (known to be present in all insect nerve cords) and not dopamine or serotonin receptors. Otherwise, the procedure is identical to that described above. and not dopamine or serotonin receptors. Otherwise, the procedure is identical to that described above.

In one embodiment, the azido-substituted octopamine agonists of the present invention are represented by the following formula (I):

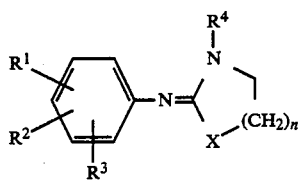

wherein
$R^1$ is azido,
$R^2$ and $R^3$ are the same or different and selected from the group consisting of hydrogen, azido, hydroxy, fluorine, bromine, chlorine, iodine, nitro, lower ($C_1$-$C_6$) alkyl, lower alkoxy, lower haloalkyl, amino, mono-lower alkyl amino, di-lower alkylamino, hydroxy substituted alkyl amino, lower acyl amino, and $R^2$ and $R^3$ may together form a fused ring,
$R^4$ is hydrogen, lower alkyl or lower alkyl substituted by hydroxy or lower alkoxy; and
n=1 or 2,
X is N, O, $CH_2$, or S; or the radiolabeled derivatives thereof such as (4-azidophenyl)imino-2-imidazolidines (X=NH, n=1); (4-azidophenyl)imino-2-pyrrolidines (X=$CH_2$, X=1); (4-azidophenyl)imino-2-oxazolidines (X=O, n=1); (4-azidophenyl)imino-2-thiazolidines (X=S, n=1) and (4-azidophenyl)imino-2-thiazines (X=S, n=2). See, e.g., the compounds in DeJong et al, *Eur. J. Pharm.* 69:175–188 (1981).

Also, in compounds of formula (I) above, $R^2$ and $R^3$ together may form a six membered phenyl, pyridine, diazine, or cyclohexyl ring fused to the noted phenyl ring. For example, the system of formula II can also be used:

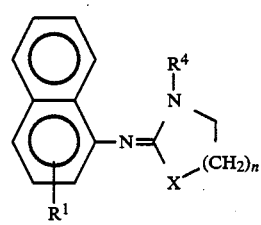

More specifically, compounds useful as octopamine agonists (1) include compounds of the formula III:

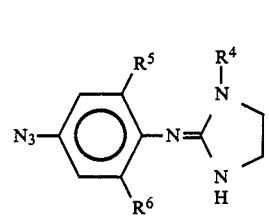

where $R^5$ and $R^6$ are $CH_3$, $C_2H_5$, i-$C_3H_7$, $C_6H_{11}$, $NH_3$, F, Cl, Br, I, $NHSO_2CH_3$, OH, H or $OCH_3$; and $R^4$ is as defined above.

Most preferably, the invention relates to an azido-substituted imidazoline derivative agonist having the formula (IV):

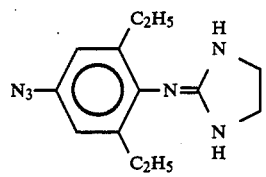

Other specific compounds include an azido-substituted imidazoline derivative of the formula (V):

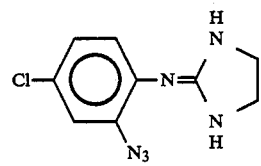

Another specific compound includes an azido-substituted imidazoline derivative of the formula (VI):

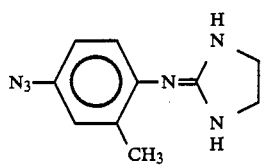

Another specific compound includes an azido-substituted imidazoline derivative of the formula (VII):

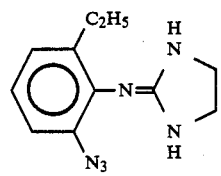

A preferable radiolabeled derivative of IV is a compound having the formula (VIII):

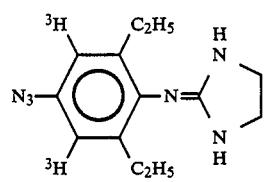

The azido-substituted formamidines of the invention are represented by the formula (IX):

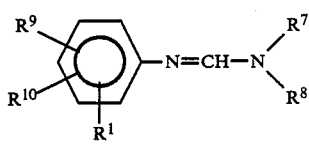

wherein
R$^1$ is azido,
R$^7$ and R$^8$ are hydrogen, $C_1$-$C_6$ alkyl or $C_1$-$C_6$ alkyl substituted by hydroxy or $C_1$-$C_6$ alkoxy;
R$^9$ and R$^{10}$ are the same or different and selected from the group consisting of hydrogen, azido, hydroxy, fluorine, chlorine, bromine, iodine, nitro, $C_1$-$C_6$ alkyl, $C_1$-$C_6$ alkoxy, $C_1$-$C_6$ haloalkyl, amino, mono The azido-substituted phenylethylamines of the invention have the following formula (X):

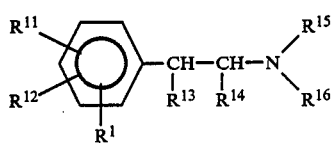

wherein
R$^1$ is azido,
R$^{11}$ and R$^{12}$ are the same or different and selected from the group consisting of hydrogen, azido, hydroxy, fluorine, chlorine, bromine, iodine, nitro, $C_1$-$C_6$ alkyl, $C_1$-$C_6$ alkoxy, $C_1$-$C_6$ haloalkyl, amino, mono- $C_1$-$C_6$ alkylamino, di- $C_1$-$C_6$ alkylamine, $C_1$-$C_6$ alkyl substituted by hydroxy, and $C_2$-$C_6$ acyl amino; and
R$^{13}$, R$^{14}$, R$^{15}$ and R$^{16}$ are the same or different and selected from the group consisting of hydrogen, $C_1$-$C_6$ alkyl, $C_1$-$C_6$ alkyl substituted by hydroxy or $C_1$-$C_6$ alkoxy.

The azido-substituted 2-benzylimidazolines of the invention have the following formula (XI):

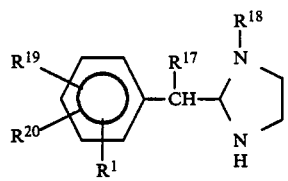

wherein
R$^1$ is azido,
R$^{18}$ is selected from the group consisting of hydrogen, $C_1$-$C_6$ alkyl and $C_1$-$C_6$ alkyl substituted by hydroxy or $C_1$-$C_6$ alkoxy; and
R$^{17}$, R$^{19}$ and R$^{20}$ are the same or different and selected from the group consisting of hydrogen, azido, hydroxy, fluorine, chlorine, bromine, iodine, nitro, $C_1$-$C_6$ alkyl, $C_1$-$C_6$ alkoxy, $C_1$-$C_6$ haloalkyl, amino, mono- $C_1$-$C_6$ alkylamino, di- $C_1$-$C_6$ alkylaminno, $C_1$-$C_6$ alkyl substituted by hydroxy, and $C_2$-$C_6$ acylamino.

The syntheses and preparation of cyclic amidines is described, for example, in Rouot et al., *J. Med. Chem.* 19:1049 (1976); Oxley et al, *J. Chem. Soc.* 497 (1947), Faust et al., *J. Org. Chem.* 26:4044 (1961); Van der Stelt et al., *Arzneim. Forsch* 15:1251 (1965) or Jen et al., *J. Med. Chem.* 15:727 (1972) and ibid. 18:90 (1975). In general, the azido compounds of the invention are prepared by preparation of the corresponding nitro derivative which is capable of being converted to an azido derivative by chemical reduction and treatment with sodium nitrite in acetic acid followed by treatment with sodium azide.

Figure 4:
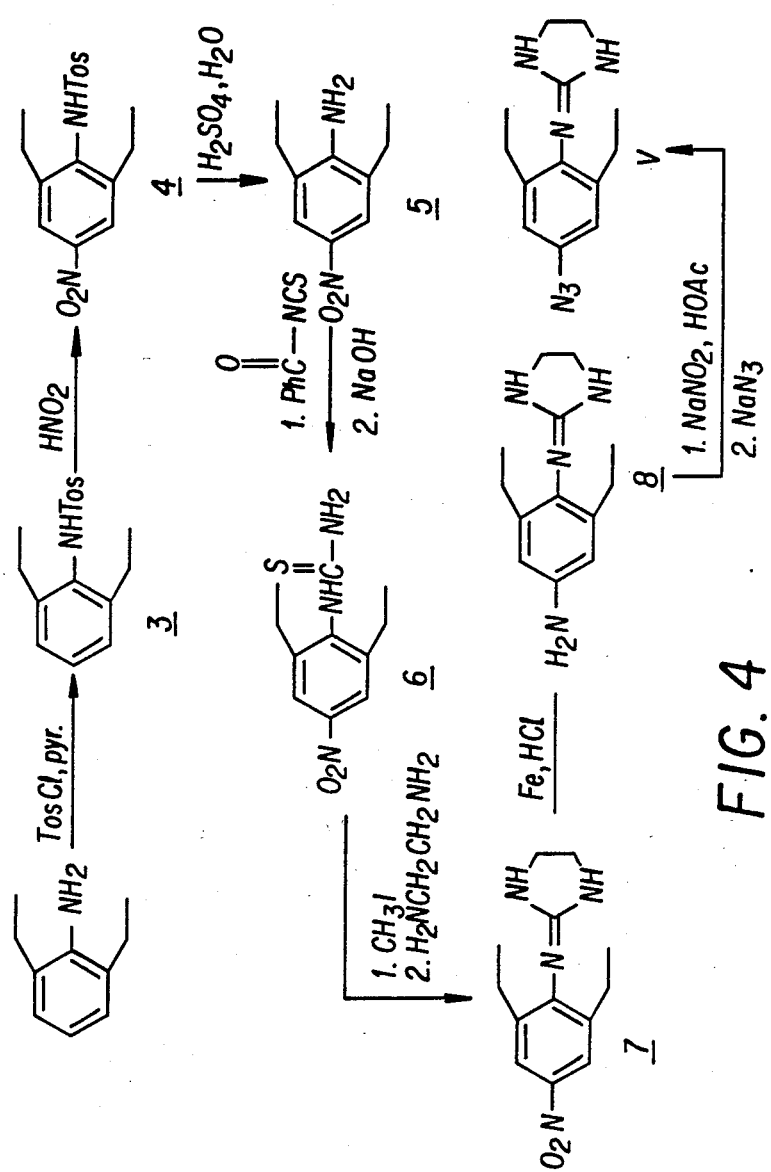
FIG. 4 depicts a method for the synthesis of (4-azido-2,6-diethylphenyl)imino-2-imidazoline (IV).

For example, azido-substituted imidazolines can be prepared from substituted anilines as follows. The scheme used for the preparation of 2-(4-azido-2,6-diethylphenyl)imino-2-imidazoline IV is depicted in FIG. 4. The amino group of 2,6-diethylanaline was protected as the p-toluenesulfonamide to give 3 then nitrated to give 2,6-diethyl-4-nitrophenyl-1-p-toluenesulfonamide 4. The protecting group was removed under acid conditions to give 5 and the amino functionality converted to the imino-imidazoline functionality by treatment with benzoyl isothiocyanate and sodium hydroxide to give 6 followed by treatment with methyl iodide and ethylenediamine to give the iminoimidazoline 7. Reduction with Fe/HCl gave the amine 8 which is converted to the azido derivative with sodium nitrite in acetic acid followed by the addition of sodium azide.

Azido-substituted formamidines may be prepared from the corresponding nitro substituted formamidine which may be synthesized by condensation of a substituted nitro analine with a disubstituted formamide dialkylacetal to give a nitro substituted formamidine. Reduction of the nitro group and treatment with sodium nitrite as described above will give the azido-substituted formamidine derivative. See Duerr, D. et al. DE 2751317 (1978); and Hollingworth, R. M., *Envir. Health Persp.* 14.57-69 (1976).

Azido-substituted phenylethylamines may be prepared, for example, from nitro-substituted phenythylamines which may be prepared from the nitro-substituted phenyl acetaldehyde or corresponding ketone by reductive amination with ammonia or a substituted amine in the presence of sodium cyanoborohydride.

Azido-substituted benylimidazolines may be prepared from a nitro-substituted phenylacetaldehyde by condensation with ethylenediamine, or substituted derivative thereof, to give a nitro-substituted benzylimidazoline. Reduction and treatment with sodium nitrite as described above will give the azido-substituted benzylimidazoline derivative.

The azido-substituted octopamine agonists of the invention can be used as pest controlling agents and as probes of the octopamine receptor. The azido group can be photolyzed with a UV light to give a nitrene moiety which irreversibly binds to nearby proteins to give a protein-agonist conjugate. The binding of the probe to the receptor allows isolation of solubilized receptors in the form of a protein-agonist conjugate by any method known to those skilled in the art, for example, by affinity chromatography or by SDS polyacrylamide gel electrophoresis. Advantageously, isolation of the receptor proteins is facilitated by use of a radiolabeled probe. Thus, the distribution and heterogeneity of endogenous receptors can be determined by monitoring for the probe in purified fractions.

Thus, this aspect of the invention relates to a method for the isolation, and subsequent characterization, of octopamine receptor proteins in an invertebrate pest comprising:

(a) bringing into contact with an octopamine receptor-bearing tissue of said pest, the radiolabeled azido-substituted octopamine agonists of the invention to form a receptor-agonist complex, (b) photolyzing said complex obtained in step (a), and thereby irreversibly binding said azido-substituted octopamine agonist to said receptor to give a protein-agonist conjugate, (c) solubilizing said protein-agonist conjugate obtained in step (b), and (d) isolating said protein-agonist conjugate.

The protein-agonist conjugate may be solubilized by, for example, treatment with a detergent such as Na dodecyl sulfate, or Triton X-100. Other reagents which may be used to solubilize the conjugate include but are not limited to Na deoxycholate, digitonin, high salt concentrations, or a combination of phenol/acetic acid/urea.

Octopamine receptor-bearing tissues which may be used in this method include, but are not limited to, the firefly lantern, locust leg muscle, brain or thoracic ganglia of *Periplaneta americana* and the ventral nerve cord or fat body of *M. sexta*. The tissues may comprise intact organs, e.g., firefly light organs, or broken cell preparations.

The molecular effects of compounds represented by Formulae I, IX, X and XI in vitro correlate with the molecular effects in vivo. However, it may be that a compound which is an excellent agonist does not show good in vivo activity. Other factors, such as possible metabolism, transport or absorption of the compound may influence its overall effectiveness. One of skill in the art, however, can by a simple preliminary trial on the desired pest ascertain quite quickly and routinely whether a chosen agent is useful in vivo.

The pest controlling agents of the present invention can be formulated as dusts, water dispersions, emulsions, and solutions. They may comprise accessory agents such as dust carriers, solvents, emulsifiers, wetting and dispersing agents, stickers, deodorants and masking agents (see, for example, *Encyclopedia of Chemical Technology,* Vol. 13, page 416 et seq.).

Dusts generally will contain low concentration, 0.1-20%, of the compounds, although ground preparations may be used and diluted. Carriers commonly include sulfur, silicon oxides, lime, gypsum, talc, pyrophyllite, bentonites, kaolins, attapulgite, and volcanic ash. Selection of the carrier can be made on the basis of compatibility with the desired pest control composition (including pH, moisture content, and stability), particle size, abrasiveness, absorbability, density, wettability, and cost. The agent of the invention alone or in combination and diluent is made by a variety of simple operations such as milling, solvent impregnations, fusing and grinding. Particle sizes usually range from 0.5-4.0 microns in diameter.

Wettable powders can be prepared by blending the agents of the invention in high concentrations, usually from 15-95%, with a dust carrier such as bentonite which wets and suspends properly in water. 1 to 2% of a surface-active agent is usually added to improve the wetting and suspendibility of the powder.

The pest-controlling agents can also be used in granules, which are pelleted mixtures of the agents, usually at 2.5-10%, and a dust carrier, e.g., adsorptive clay, bentonite or diatomaceous earth, and commonly within particle sizes of 250 to 590 microns. Granules can be prepared by impregnations of the carrier with a solution or slurry of the agents and can be used principally for mosquito larvae treatment or soil applications.

The agents can also be applied in the form of an emulsion, which comprises a solution of the agents in water immiscible organic solvents, commonly at 15-50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum factions, methylisobutylketone and amyl acetate. Water emulsion sprays from such emulsive concentrates can be used for plant protection and for household insect control.

The agents can also be mixed with baits, usually comprising 1-5% of agents with a carrier especially attractive to insects. Carriers include sugar for house flies, protein hydrolysate for fruit flies, bran for grasshoppers, and honey, chocolate or peanut butter for ants.

The agents can be included in slow release formulations which incorporate non-persistent compounds, insect growth regulators and sex pheromones in a variety of granular microencapsulated and hollow fiber preparations.

The pest controlling agents of the present invention may be applied depending on the properties of the particular pest controlling compound, the habits of the pest to be controlled and the site of the application to be made. It can be applied by spraying, dusting or fumigation.

Doses of the weight of the ingredients may typically vary between 0.001-100 lbs/acre, preferably between 0.001-5 lbs/acre.

Sprays are the most common means of application and generally will involve the use of water as the principal carrier, although volatile oils can also be used. The pest-control agents of the invention can be used in dilute sprays (e.g., 0.001-10%) or in concentrate sprays in which the composition is contained at 10-98%, and the amount of carrier to be applied is quite reduced. The use of concentrate and ultra low volume sprays will allow the use of atomizing nozzles producing droplets of 30 to 80 microns in diameter. Spraying can be carried out by airplane or helicopter.

Aerosols can also be used to apply the pest controlling agents. These are particularly preferred as space sprays for application to enclosures, particularly against flying insects. Aerosols are applied by atomizing amounts of a liquified gas dispersion or bomb but can be generated on a larger scale by rotary atomizers or twin fluid atomizers.

A simple means of pest control agent dispersal is by dusting. The pest controlling agent is applied by introducing a finely divided carrier with particles typically of 0.5-3 microns in diameter into a moving air stream.

Any octopamine-receptor containing pest is treatable by the formulation of the present invention. These pests include all invertebrate pests, including, but not limited to, round worms (e.g., hookworm, trichina, ascaris); flatworms (e.g., liver flukes and tapeworms); jointed worms (e.g., leeches); molluscs (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies); plecoptera; mallophaga (biting lice); thysanoptera; and siphonaptera (fleas); dictyoptera (roaches); psocoptera (e.g., booklice); and certain hymenoptera (e.g., those whose larva feed on leaves).

Having now generally described this invention, the same will become better understood by reference to certain specific examples which are included herein for purposes of illustration only and are not intended to be limiting unless otherwise specified.

EXAMPLES

EXAMPLE 1

Synthesis of (4-azido-2,6-diethylphenyl)imino-2-imidazoline

A. Preparation of 2,6-Diethylphenyl-p-toluenesulfonamide

To 29.85 g (0.200 mol) of 2,6-diethylaniline in 100 ml of pyridine was added 41.94 g (0.220 mol) of p-toluenesulfonyl chloride in portions at 10° to 4° C. The reaction mixture was stirred overnight, poured into 1 l of 10% hydrochloric acid, filtered, washed three times with water, dissolved in $CHCl_3$, dried over $MgSO_4$, and evaporated to dryness to yield 61.48 g (101.3%) of crude product. A portion (46.3 g) was recrystallized from cyclohexane to yield 33.1 g of 2,6-diethylphenyl-p-toluenesulfonamide, mp. 133.4°. NMR ($CDCl_3$): δ 1.05 (t, 6H), 2.45 (m, 7H), 6.10 (s, 1H), 6.9–7.3 (m, 5H), 7.5–7.7 (d, 2H).

B. Preparation of 2,6-Diethyl-4-nitrophenyl-p-toluenesulfonamide

To 13 ml of 70% nitric acid in 100 ml of water was added 15.17 g (50.0 mmol) of the -toluenesulfonate obtained in step A, followed by the addition of 100 ml of glacial acetic acid and 0.37 g (5.0 mmol) of sodium nitrite. The mixture was heated on a steam bath for 1.5 hrs, cooled, diluted with 250 g of ice, and the precipitate was collected to yield 8.82 g of crude product. The crude product was chromatographed on 300 g of silica gel with 5:1 and 3:1 hexane:ethyl acetate to yield 6.30 g (36.2%) of 2,6-diethyl-4-nitrophenyl-p-toluenesulfonamide. NMR ($CDCl_3$):δ 1.10 (t, 6H), 2.5 (m, 7H), 6.5 (s, 1H), 7.2–7.7 (dd, 4H), 7.97 (s, 2H).

C. Preparation of 2,6-Diethyl-4-nitroaniline

To 6.28 g (18.0 mmol) of the nitro derivative obtained in step B was added a solution of 2 ml of water and 20 ml of conc. $H_2SO_4$. The mixture was then heated on a steam bath for 15 min, cooled in ice, diluted with 150 ml of water, made basic with 50% NaOH solution, and the precipitate filtered and washed with water. The solids were then dissolved in chloroform, dried over $Na_2SO_4$, and the solvent was evaporated to yield 3.16 g (90.3%) of 2,6-diethyl-4-nitroaniline. NMR ($CDCl_3$):δ 1.30 (t, 6H), 2.50 (q, 4H), 4.35 (b, 2H), 7.90 (s, 2H).

D. Preparation of 2,6-Diethyl-4-nitrophenylthiourea

To 2.34 g (24.1 mmol) of potassium thiocyanate in 30 ml of acetone was added 2.32 ml (20.0 mmol) of benzoyl chloride. The mixture was then refluxed for 15 min, cooled to r.t., and 3.16 g (16.3 mmol) of 2,6-diethyl-4-nitroaniline obtained from step C was added. The mixture was then refluxed for 15 min, cooled to r.t., and poured into 200 ml of ice-water. The precipitate was collected and washed with water, then dissolved in a solution comprising 0.70 g (18 mmol) of sodium hydroxide in 5 ml of water and 50 ml of ethanol. The solution was refluxed for 1 hr, cooled to r.t., poured into icewater, then the precipitate was collected, washed with water several times, and dried. The solids were then triturated with ethyl acetate to yield 2.44 g (59.2%) of product. NMR ($CDCl_3$, $d_6$-DMSO):δ 1.30 (t, 6H), 2.74 (q, 4H), 6.9 (b, 2H), 7.98 (s, 2H), 9 (b, 1H).

E. Preparation of (2,6-Diethyl-4-nitrophenyl)imino-2-imidazolidine

To 5.066 g (20.0 mmol) of 2,6-diethyl-4-nitrophenylthiourea in 50 ml of methanol was added 1.25 ml (20.0 mmol) of methyl iodide. The mixture was refluxed for 4 hrs, then evaporated to dryness. To the dried residue was added 8.00 ml (0.12 mole) of ethylenediamine (freshly distilled from calcium hydride) and 8 ml of abs. ethanol. The solution was refluxed for 17 hrs, then poured onto ice. The semisolid was triturated with water twice, then taken up in ethyl acetate and washed with water and saturated salt solution. The solution was dried over sodium sulfate, evaporated to dryness, and the residue chromatographed on 150 g of silica gel by elution with 400 ml chloroform, followed by 1% triethylamine (TEA) in methanol. 2,6-(Diethyl-4-nitrophenyl)imino-2-imidazoline was eluted by 1% TEA in methanol to give 0.527 g (10.0%). NMR ($CDCl_3$):δ 1.25 (t, 6H), 2.62 (q, 4H), 3.50 (s, 4H), 4.80 (b, 2H), 7.90 (s, 2H). A second product having the following formula: was also eluted to give 3.054 g (54.7%). NMR ($CDCl_3$):δ 1.24 (t, 6H), 2.55 (q, 4H), 2.86 (t, 2H), 3.30 (t, 2H), 7.91 (s, 2H); NH is a broad hump from ca. 1 to 5.5.

F. Preparation of (4-Amino-2,6-diethylphenyl)imino-2-imidazolidine (PA-NC-5)

To 286 mg (1.09 mmole) of (2,6-diethyl-4-nitrophenyl)imino-2imidazoline obtained from step E and 391 mg (7.00 mmole) of iron filings suspended in 2.5 ml of 50% w/w aq. ethanol at reflux was added 1.3 ml (2.5 mmole) of a hydrochloric acid solution comprising 5.00 ml of conc. HCl diluted to 31 ml with 50% w/w aq. ethanol. The mixture was refluxed for 0.5 hr, cooled to 30°, and 2.5 ml of 1.00N sodium hydroxide solution was added. The mixture was then filtered and the filtrate was evaporated to dryness, triturated with ethanol, evaporated, and taken up in 20% methanol in ethyl acetate. The crude product was then chromatographed on 60 g of silica gel with 20% methanol in ethylacetate to yield 174 mg (68.8%) of 2-(4-amino-2,6-diethylphenyl)imino-2-imidazoline. NMR ($CDCl_3$):δ 1.12 (t, 6H), 2.45 (q, 4H), 3.68 (dq, 4H), 5.3 (b, 1H), 6.33 (s, 2H), 8.82 (b, 1H), 9.86 (b, 1H).

G. Preparation of (4-Azido-2,6-diethylphenyl)imino-2-imidazolidine (IV)

To 166 mg (0.715 mmol) of (4-amino-2,6-diethylphenyl)imino-2-imidazoline obtained from step F in 10 ml of 3M acetic acid at 4° C. was added 50 mg (0.72 mmole) of sodium nitrite in 1 ml of water. After 3 min., a solution of 55 mg (0.85 mmole) of sodium azide in 1 ml of water was added and the solution was stirred at 2° to 4° C. for 10 min. The solution was then made basic with 50% sodium hydroxide and diluted with ether. The organic layer was washed three times with water, once with saturated salt solution, dried over sodium sulfate, and evaporated to dryness to yield 148 mg of crude product. The material was chromatographed on two 1 mm Analtech silica gel GF plates with 2% triethyl amine in methanol to yield 115 mg (62.2%) of product. The analytical sample was recrystallized from ether to yield pale yellow crystals, mp 157.6° (dec.). NMR (CDCl$_3$):δ 1.16 (t, 6H), 2.50 (q, 4H), 3.40 (s, 4H), 5.10 (b, 2H), 6.66 (s, 2H). IR(CHCl$_3$): 3450, 2105, 1675 cm$^{-1}$. MS (EI), m/e 258 (M+).

Anal. Calcd. for C$_{13}$H$_{18}$N$_6$: C, 60.44; H, 7.02; N, 32.53. Found: C, 59.93; H, 6.98; N, 32.16.

EXAMPLE 2

Figure 2:
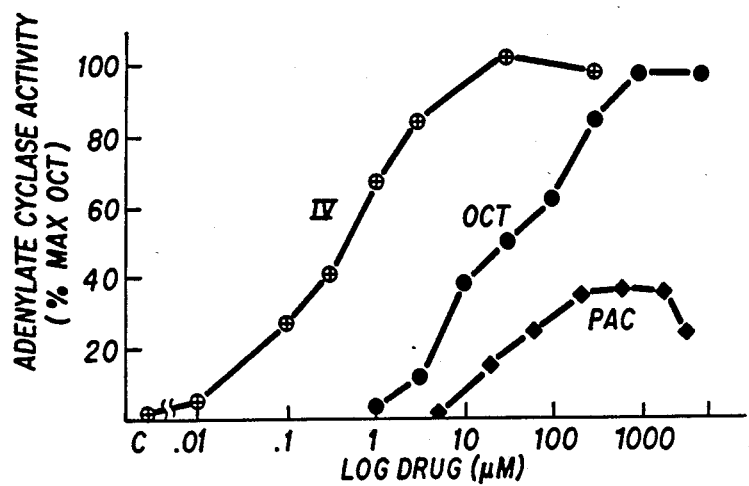
FIG. 2 depicts a graph of adenylate cyclase activity for various dosages of (4-azido-2,6-diethylphenyl)imino-2-imidazoline (IV), octopamine, and (4-azido-2,6-dichlorophenyl)imino-2-imidazoline (PAC).

Test of (4-Azido-2,6-Diethylphenyl-2-Imidazoline (IV) Under Reversible Conditions (4-Azido-2,6-diethylphenyl)-2-imidazoline (IV) was first tested under conditions (in dim light) in which the azido group remains intact and in which binding remains reversible. Since it had been previously shown that the firefly light organ is a highly specific and sensitive assay system for detecting octopaminergic compounds (Nathanson, J. A., in "Insect Neurochemistry and Neurophysiology," Borkovec, A., et al.. eds., Humana, Clifton, N.J., 1986; pp. 263–266), the ability of (4-azido-2,6-diethylphenyl)-2-imidazoline (IV) to activate adenylate cyclase in membrane preparations of this tissue was tested. FIG. 2 shows that this compound (IV) was not only a full agonist but was extremely potent, indeed the most potent octopamine agonist yet described in this system. Significant stimulation of enzyme activity was detectable at a concentration of 20 nanomolar of the azido compound (IV) or less. The calculated K$_a$ ranged from 0.35 to 0.7 micromolar, or about 100-fold more potent than octopamine itself. The azido compound was almost 1000-fold more potent than the commercial ligand (4-azido-2,6-dichlorophenyl-)imino-2-imidazoline (PAC) available from New England Nuclear. See Kawahara, R., et al.. Eur. J. Pharm. 117:43–50 (1985).

EXAMPLE 3

Test of (4-Azido-2,6-Diethylphenyl)imino-2-Imidazoline (IV) In the Presence of Antagonists Stimulation of adenylate cyclase by compound IV could be inhibited by several antagonists which have shown selectivity for octopamine receptors, including phentolamine, cyproheptadine, and mianserin. The beta-adrenergic antagonist, propranolol, was less potent. The calculated K$_i$ and relative potency of these various blockers in inhibiting compound IV stimulation was quite similar to that for these same compounds in inhibiting stimulation by formamidine, DCDM, or by octopamine (Table 1). These data supported the above evidence that compound IV is a potent octopamine receptor agonist.

TABLE 1

| Calculated K$_i$ Values for Antagonists Inhibiting Stimulation of Light Organ Adenylate Cyclase By Either Octopamine, DCDM (a Formamidine) or Compound IV | | | |
|---|---|---|---|
| | K$_i$ | | |
| ANTAGONIST | OCT | DCDM | IV |
| Mianserin | 0.6 | — | 0.9 |
| Cyproheptadine | 6 | 2 | 5 |
| Phentolamine | 46 | 18 | 20 |
| Propranolol | 175 | 50 | 75 |

EXAMPLE 4

Figure 3:
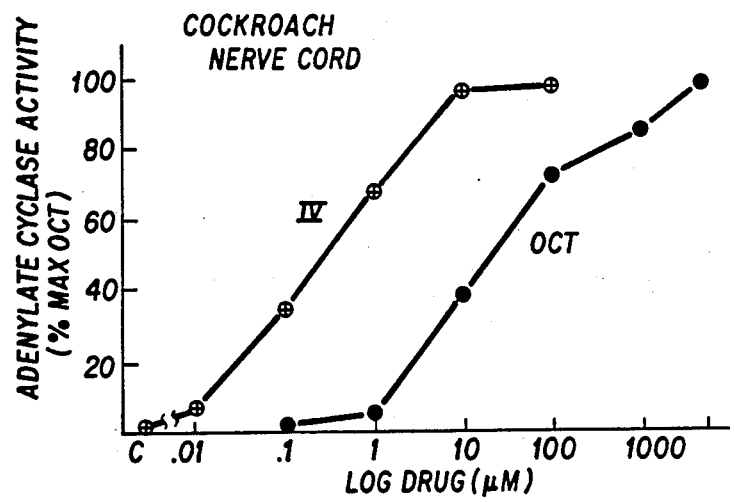
FIG. 3 depicts a graph of adenylate cyclase activity in cockroach nerve cord for various dosages of (4-azido-2,6-diethylphenyl)imino-2-imidazoline (IV) and octopamine.
Figure 5:
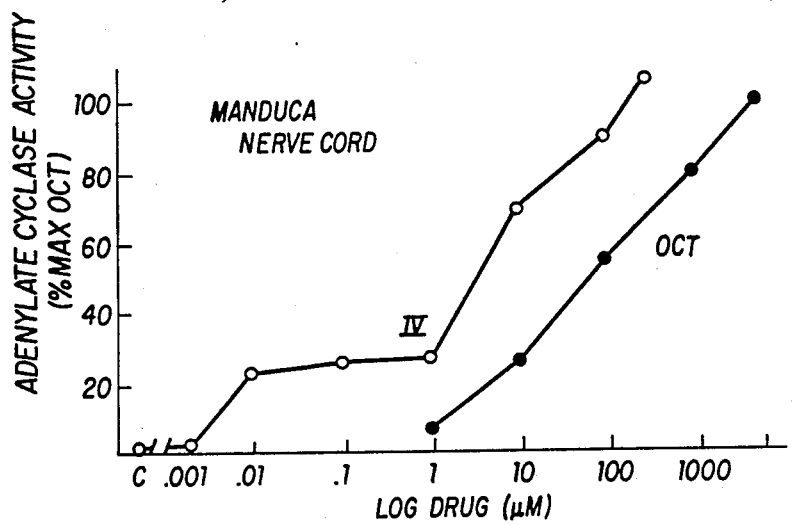
FIG. 5 depicts a graph of adenylate cyclase activity (% max. oct.) in *Manduca sexta* nerve cord for various dosages of (4-azido-2,6-diethylphenyl)imino-2-imidazoline (IV) and octopamine.

Test of (4-Azido-2,6-Diethylphenyl)imino-2-Imidazoline (IV) With Other Tissues and Species Preliminary screening studies showed that compound IV was potent not only in the firefly but also in other tissues and species known to contain octopamine receptors. In cockroach nerve cord, in which formamidines are notably poor simulators of adenylate cyclase (Nathanson, J. A., Mol. Pharmacol. 28:254–268 (1985)), compound IV was more than 60-fold more potent than octopamine (FIG. 3). In cockroach leg muscle, compound IV was 100-fold more potent than octopamine (data not shown). In Manduca sexta nerve cord, compound IV appeared to show a diphasic response (FIG. 5), suggesting that it was stimulating both the high affinity receptor previously detected by NC-7 (Nathanson, J. A., Mol. Pharmacol. 28:254–268 (1985)) and the formamidines (Hollingworth and Lund, in "Insecticide Mode of Action," Coats, J. R., ed., Academic Press, NY, 1982, pp. 189–227; Hollingworth and Johnstone, in "IUPAC Pesticide Chemistry," Miyamoto et al., eds., Pergamon Press, New York, 1983, pp. 187–192) as well as a lower affinity receptor previously detected by NC-5. From these studies as well as those in the firefly light organ (a tissue derived from fat cells), it appears that compound IV has a broad range of activity in octopaminergic receptor tissues. This supplies additional evidence that compound IV should be useful in isolating octopamine receptors from a wide variety of tissues and species.

EXAMPLE 5

In Vivo Activity of (4-Azido-2,6-Diethylphenyl)imino-2-Imidazoline (IV)

Figure 6:
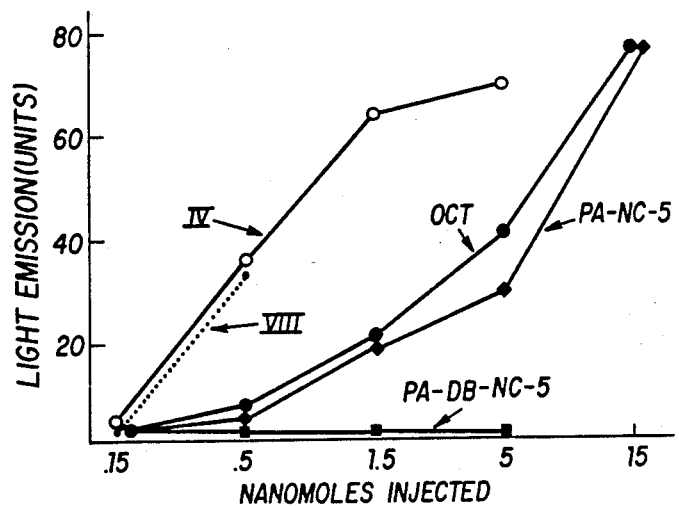
FIG. 6 depicts a graph of light emission of an intact firefly light organ for various injected amounts of compound IV, tritiated compound IV (VIII), octopamine, PA-NC-5 ((p-amino-2,6-diethylphenyl) imino-2-imidazoline) and PA-DB-NC-5 ((p-amino-3,5-dibromo-2,6-diethylphenyl)imino-2-imidazoline).
Figure 7:
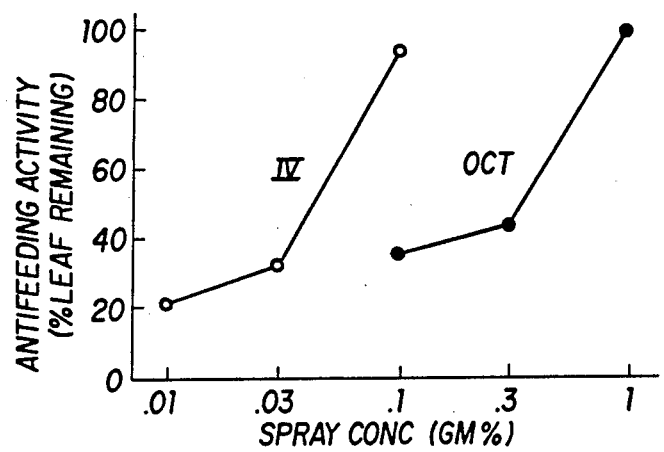
FIG. 7 depicts a graph of antifeeding activity of Manduca larvae (% leaf remaining) for various spray concentrations of compound IV and octopamine.

In addition to being active in broken cell preparations, compound IV was also potent in stimulating light emission when injected into isolated firefly tails under conditions in which presynaptic release was blocked (previous studies have indicated that octopamine receptors located postsynaptically in the light organ mediate neural control of light emission in the firefly). As shown in FIG. 6, compound IV was a full agonist of the light organ and about 15-fold more potent than octopamine. In other studies (FIG. 7), compound IV was found to be about 10-fold more potent than octopamine in inhibiting feeding of Manduca larvae, as measured by the percentage of leaf area remaining after 72 hours of feeding (in dim light) on tomato leaves sprayed with various concentrations of the compound. Observations made during this experiment indicated that compound IV elicited behavioral changes (hyperactivity, tremor, rearing, walk-off) similar to those seen with octopamine and other octopaminergic compounds such as the non-azido-substituted formamidines. These results reinforce the concept that octopamine agonists have potential use as leaf protectants.

EXAMPLE 6

Irreversible Activation of Adenylate Cyclase by (4-Azido-2,6-Diethylphenyl)imino-2-Imidazoline (IV)

Figure 8:
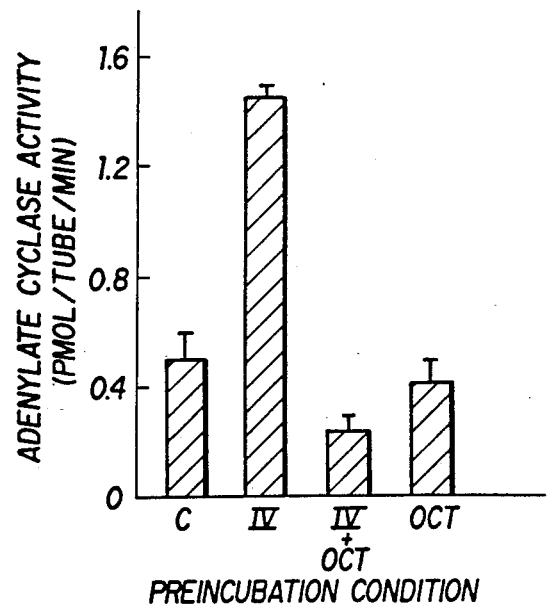
FIG. 8 depicts a bar graph of adenylate cyclase activity for a control sample of firefly organ membranes, a photolyzed sample containing compound IV, a photolyzed sample containing compound IV and octopamine, and a photolyzed sample containing octopamine.

The UV absorption spectrum of compound IV shows peaks at 210 and 255 nm. When exposed to ultraviolet light in these wavelengths, the N$_3$ azido group on the para-position is photolyzed to yield free N$_2$ and a highly with a number of protein sites, including areas with double covalently with a number of protein sites, including areas with double bonds, amino groups and -carboxylic acids. If compound IV is occupying an octopamine receptor at the time of photolysis, then the ligand will bind to a site on or near the receptor protein. A priority was not possible to predict if this covalent binding would lead to an active or an inactive receptor. To determine this, a series of photolysis experiments were performed in which firefly light organ membranes were preincubated with or without compound IV and then photolyzed. Next, the membranes were extensively washed to remove all free ligand and any ligand that was not covalently bound. Following this, adenylate cyclase activity was assayed. FIG. 8 shows that prior photolysis with compound IV led to a 3-fold increase in adenylate cyclase activity, suggesting that a proportion of the octopamine receptors had been irreversibly bound and were being activated. Evidence that this was due to receptor activation (as opposed to a direct effect on adenylate cyclase) was shown by the fact that the irreversible stimulation could be blocked (third bar of graph) if, during the preincubation, compound IV was incubated together with an excess of octopamine. Presumably, the excess octopamine displaced compound IV so that, when the membranes were later photolyzed, octopamine (and not compound IV) was occupying the receptor. Subsequently, during washing, the octopamine was removed so that the receptor returned to its unstimulated state. (As would be expected, preincubation with octopamine alone [fourth bar of the graph] failed to cause any irreversible activation since it was washed out.)

EXAMPLE 7

Radioactive Labeling of (4-Azido-2,6-Diethylphenyl)imino-2-Imidazoline (IV)

Figure 9:
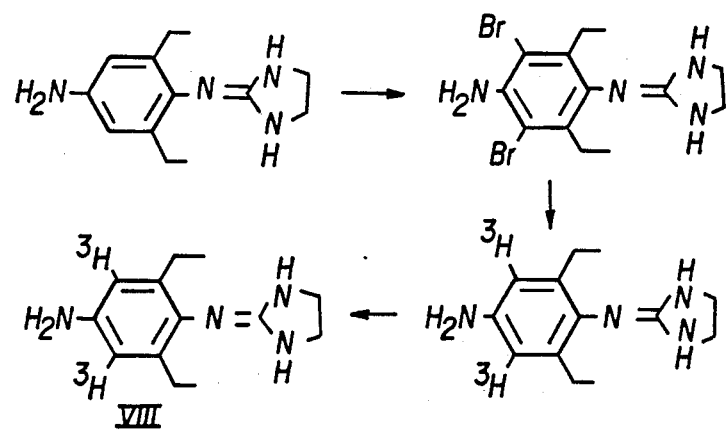
FIG. 9 depicts the scheme used for the synthesis of 2-(4-azido-2,6-diethyl-3,5-ditritiophenyl)imino-2-imidazoline (VIII)

In order to use compound IV to identify and isolate octopamine receptors, a method of labeling the compound radioactively was devised. Unfortunately, because of the liability of the azido group, compound IV could not itself be labeled directly using such methods as tritium exchange, since these methods would reduce the azido group. Instead, the scheme depicted in FIG. 9 was devised. This scheme required the synthesis of a new precursor, (p-amino-3,5-dibromo-2,6-diethylphenyl)imino-2-imidazoline (PA-DB-NC-5). This precursor was then reduced in the presence of tritium gas to form (p-amino-2,6-diethylphenyl)imino-2-imidazoline, radioactively labeled at the 3- and 5-positions. After purification, this latter compound was then converted to compound VIII bearing tritium in the 3- and 5-positions, and then purified by thin layer chromatography (TLC).

EXAMPLE 8

Figure 10:
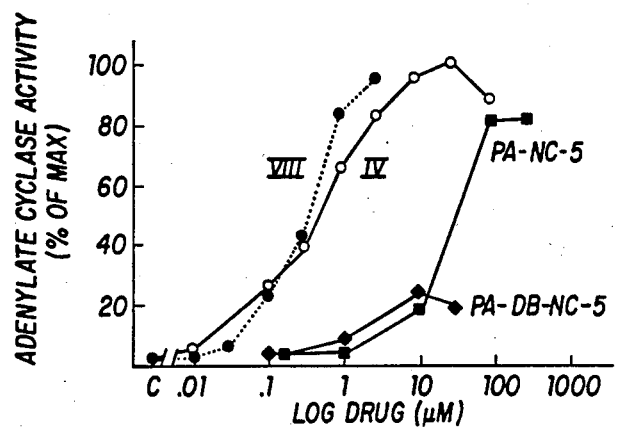
FIG. 10 depicts a graph of adenylate cyclase activity (% max. oct.) for various concentrations of VIII, IV, PA-NC-5 ((p-amino-2,6-diethylpheny)imino-2-imidazoline) and PA-DB-NC-5 ((p-amino-3,5-dibromo-2,6-diethylphenyl)imino-2-imidazoline).

Verification of the Identity and Biological Activity of Tritiated Compound VIII Although the labeled compound appeared as a single spot on TLC, two separate verification procedures were utilized to provide additional evidence as to the activity of compound VIII. In the first procedure, the ability of the labeled compound to activate adenylate cyclase in light organ membranes was measured. FIG. 10 shows that the activity profile of tritiated compound VIII was virtually identical to that of genuine, unlabeled IV. FIG. 10 also shows that the other possible products of the reaction, (p-amino-3,5-dibromo-2,6-diethylphenyl)imino-2-imidazoline (PA-DB-NC-5) and (p-amino-2,6-diethylphenyl)imino-2-imidazoline (PA-NC-5), were markedly different in their activity profiles, indicating that, had they contaminated the tritiated product substantially, this would have been easily picked up by a decrease in the apparent activity of tritiated product.

In the second verification procedure, a bioassay was conducted which measured the effect of tritiated VIII on eliciting light emission when injected into isolated firefly tails. FIG. 6 shows that injection of 0.5 nmoles of the labeled compound (the highest dose tested caused a light response identical to that due to injection of the genuine unlabeled compound. As with the adenylate cyclase experiment (FIG. 10), the other possible products of the reaction, (p-amino-3,5-dibromo-2,6-diethylphenyl)imino-2-imidazoline (PA-DB-NC-5) and (p-amino-2,6-diethylphenyl)imino-2-imidazoline (PA-NC-5), were much less active. Taken together, these two assays provide strong evidence that the labeled compound VIII is identical to unlabeled IV and is potent biologically.

EXAMPLE 9

Reversible Binding of Compound VIII to Membranes

The low affinity of octopamine for its receptor ($K_a = 30$ micromolar) results in a half-time of dissociation of considerably less than 0.1 second. This precludes the use of labeled octopamine as a receptor ligand since the time required for the separation of free from bound ligand during a filtration assay is several seconds. On the other hand, the much higher affinity of IV for the octopamine receptor ($K_a$ about 0.5 micromolar) results in an off-time of a few seconds, making ligand binding experiments via filtration just barely feasible. In other words, following washing, enough ligand will still be on the receptor to allow estimation of the receptor's binding constant for compound IV. (Because there will still be significant loss of label during filtration, one cannot use this type of assay to estimate total receptor number).

Figure 11:
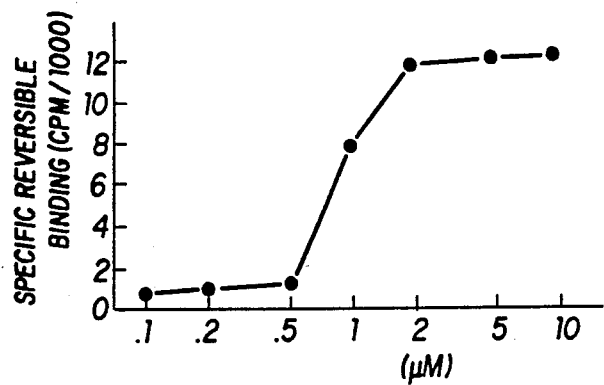
FIG. 11 depicts a graph of specific binding of VIII to firefly light organ membranes for various concentrations of VIII.

FIG. 11 shows the results of a binding experiment in which compound VIII binding to light organ membranes was measured in the absence or presence of a 1000-fold excess of mianserin (a potent antagonist of octopamine binding—see Table 1 above) for various concentrations of compound VIII. The difference in the amount of binding in the absence and presence of mianserin represents the specific binding. It can be seen that, typical of a specific receptor interaction, this binding saturates at a low concentration of about 2 micromolar, similar to the concentration required for a $V_{max}$ stimulation of adenylate cyclase by compound VIII (see FIG. 2). Furthermore, 50% binding occurs at about 0.8 micromolar, again similar to the $K_a$ of about 0.5 micromolar observed when compound VIII stimulates adenylate cyclase. These results support our adenylate cyclase data indicating that compound VIII binds with high affinity to octopamine receptors.

EXAMPLE 10

Irreversible Binding of Compound VIII to Membranes

Figure 12:
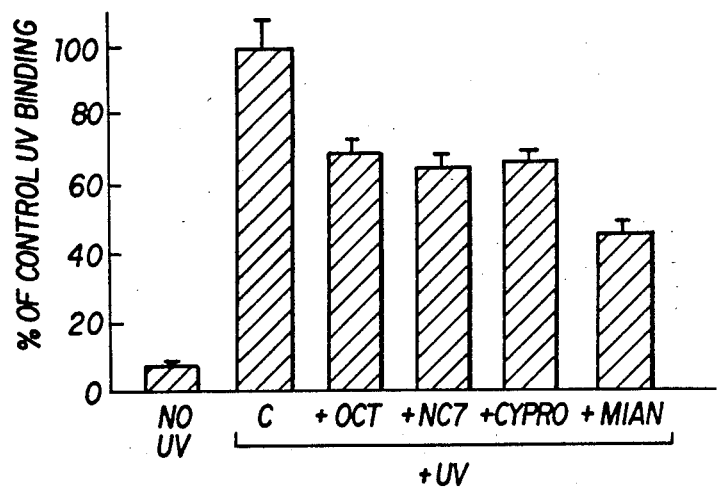
FIG. 12 depicts a bar graph showing the amount of irreversible binding to firefly light organ membranes with VIII, with and without UV light and various displacing reagents including octopamine, (2-methyl-4-chlorophenyl)imino-2-imidazoline (NC7), cyproheptadine (CYPRO), and mianserin (MIAN).

With the labeled receptor probe in hand, a series of experiments were conducted in which irreversible binding to firefly light organ membranes was demonstrated. In these experiments, membranes were preincubated with the probe for under various conditions and then the mixture was photolyzed in quartz microcuvettes using a UV-C germicidal lamp. Carrier protein was added and the free (unbound) label removed by either extensive washing on glass fiber filters or by repeated TCA precipitation, NaOH solubilization and washing in test tubes (the latter procedure gave lower blanks). FIG. 12 shows that exposure to UV light caused a 14-fold increase in the amount of label permanently bound. To determine whether the binding was specific, various displacing agents were added during the preincubation with tritiated IV (VIII), and the mixture then photolyzed. As shown on FIG. 12, octopamine or the synthetic octopaminergic compound, NC-7, displaced between 30 and 35% or the binding. The octopaminergic antagonist, cyproheptadine, displaced about 35% and the most potent octopaminergic antagonist known, mianserin, displaced binding by about 55%. In other experiments, it was found that binding is not displaced with nonoctopaminergic compounds such as dopamine, serotonin, norepinephrine, or histamine. These data provide additional evidence that tritiated IV (VIII) is labeling the octopamine receptors.

EXAMPLE 11

Autoradiographic Studies

Because compound VIII binds irreversibly, it should have potential as an anatomic probe to historically localize octopamine receptors at the light microscopic level. To determine if this is feasible, some preliminary studies were conducted using intact isolated firefly light organs. The lanterns were first preincubated with VIII in dim light and then exposed either to no light or to intense UV. Following this step, the lanterns were extensively washed, then slide mounted, dehydrated, and exposed to tritium-sensitive X-ray film. After development, the film shows that UV light caused marked labeling of the lantern. In the absence of UV light, there was no labeling. Localization of octopamine receptors, particularly in the nervous system, should aid in an understanding of how octopamine exerts its behavioral effects in insects.

EXAMPLE 12

Receptor Isolation Studies

Once compound VIII is bound, it is possible to solubilize the octopamine receptors (and other membrane proteins) with detergent and identify and isolate them on SDS-polyacrylamide gels. In preliminary studies, it has been possible to solubilize, separate, and identify proteins which irreversibly bind compound VIII after photolysis of light organ membranes. FIG. 13, lane A, shows a densitometry scan of an autoradiogram of these proteins separated on an SDS-polyacrylamide gel. Four major labeled peaks can be seen, and their molecular weights can be estimated from the series of radioactive MW standards in lane D. It can be seen that, in the absence of UV radiation (Lane C), no proteins were labeled. In lane B, the membranes were photolyzed as in lane A, except that an excess of the octopamine antagonist, mianserin, was present. It can be seen that mianserin completely blocked labeling of the peak at MW 74,000, indicating that this protein peak represents an octopamine receptor protein(s).

From the point of view of developing octopaminergic pesticides, it will be of utmost importance to determine the distribution of octopamine receptor protein(s) among various insect species and, within species, in various tissues and between larval and adult forms. Use of azido compound VIII as a receptor probe will allow determination of the distribution of octopamine receptor proteins.

Although the foregoing invention has been described by way of illustration and example for purposes of clarity and understanding, it will be obvious that certain changes and modifications may be practiced within the scope of the invention, as limited only by the scope of the appended claims.

What is claimed is:

1. An azido-substituted octopamine agonist of the formula:

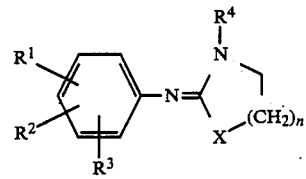

wherein
$R^1$ is azido,
$R^2$ and $R^3$ are the same or different and selected from the group consisting of hydrogen, azido, hydroxy, fluorine, bromine, chlorine, iodine, nitro, lower ($C_1$-$C_6$) alkyl, lower ($C_1$-$C_6$) alkoxy, lower haloalkyl, amino, mono-lower alkyl amino, di-lower alkyl amino, hydroxy substituted alkyl amino, lower acyl amino, and $R^2$ and $R^3$ may together form a fused ring;
$R^4$ is hydrogen, lower alkyl or lower alkyl substituted by hydroxy or lower alkoxy;
$n = 1$ or 2;
$X$ is NH, O, $CH_2$, or S; and
wherein the ratio $K_a^{oct}/K_a^{(Azido)}$ for said azido-substituted octopamine agonist, as determined in a broken cell preparation of the firefly light organ, is greater than 1;
with the proviso that wherein $R^2$ is fluorine, bromine, chlorine or iodine, then $R^3$ is selected from the group consisting of hydrogen, nitro, lower ($C_1$-$C_6$) alkyl, lower ($C_1$-$C_6$) alkoxy, lower haloalkyl, amino, mono-lower alkyl amino, di-lower alkyl amino, hydroxy substituted alkyl amino, and lower acyl amino.

2. The azido-substituted octopamine agonist of claim 1, wherein the ratio $K_a^{oct}/K_a^{(Azido)}$ is greater than 10.

3. An azido-substituted octopamine agonist of the formula:

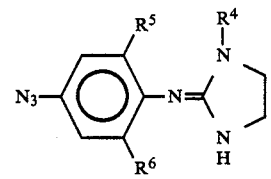

wherein
$R^5$ and $R^6$ are the same or different and selected from the group consisting of $CH_3$, $C_2H_5$, i-$C_3H_7$, $C_6H_{11}$, $NH_3$, F, Cl, Br, I, $NHSO_2CH_3$, OH, H and $OCH_3$;
$R^4$ is hydrogen, lower alkyl, or lower alkyl substituted by hydroxy or lower alkoxy; and wherein the ratio $K_a{}^{oct}/K_a{}^{(Azido)}$ for said azido-substituted octopamine agonist, as determined in a broken cell preparation of the firefly light organ, is greater than 1; with the proviso that wherein $R^2$ is fluorine, bromine, chlorine or iodine, then $R^3$ is selected from the group consisting of hydrogen, nitro, lower ($C_1$–$C_6$) alkyl, lower ($C_1$–$C_6$) alkoxy, lower haloalkyl, amino, mono-lower alkyl amino, di-lower alkyl amino, hydroxy substituted alkyl amino, and lower acyl amino.

4. The azido-substituted octopamine agonist of claim 3, wherein the ratio $K_a{}^{oct}/K_a(Azido)$ is greater than 10.

5. An azido-substituted octopamine agonist having the formula:

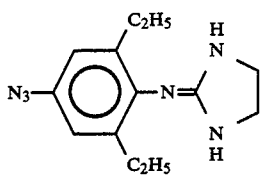

6. An azido-substituted octopamine agonist having the formula:

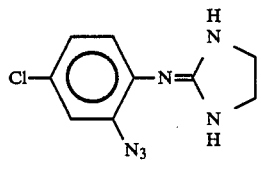

7. An azido-substituted octopamine agonist having the formula:

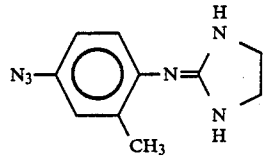

8. An azido-substituted octopamine agonist having the formula:

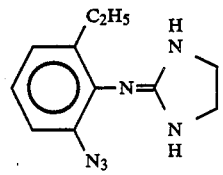

9. The azido-substituted octopamine agonist of claim 1 wherein said agonist is radiolabeled.

10. An invertebrate pest-controlling composition comprising an invertebrate pest-controlling amount of the azido-substituted octopamine agonist of claim 1 together with a pesticidally inert carrier.

11. The composition of claim 10, wherein said carrier is selected from the group consisting of sulfur, silicon oxides, lime, gypsum, talc, pyrophyllite, bentonite, kaolins, allapulgite and volcanic ash.

12. The composition of claim 10 in the form of a dust, a granule, pellet or aerosol.

13. A method of controlling an invertebrate pest comprising bringing into contact with said pest an invertebrate pest-controlling amount of the azido-substituted octopamine agonist of claim 1.

14. A method of controlling an invertebrate pest comprising
(a) bringing said pest into contact with the azido-substituted octopamine agonist of claim 1 in an amount sufficient to effect control of said pest when exposed to UV light of wavelength 210 to 310 nm of intensity sufficient to penetrate the exoskeleton of said pest, and for a time sufficient to allow said agonist to complex with the octopamine receptors of said pest, and
(b) exposing said pest to UV light to cause the formation of an agonist-receptor conjugate to irreversibly activate adenylate cyclase.

* * * * *

UNITED STATES PATENT AND TRADEMARK OFFICE
CERTIFICATE OF CORRECTION

PATENT NO. : 4,892,871

DATED : January 9, 1990

INVENTOR(S) : J. A. Nathanson

It is certified that error appears in the above-identified patent and that said Letters Patent is hereby corrected as shown below:

At column 1, line 5, the patent should read as follows:

--STATEMENT AS TO RIGHTS TO INVENTIONS MADE UNDER FEDERALLY SPONSORED RESEARCH AND DEVELOPMENT

This invention was made with government support under DOA8600090 awarded by the U.S. Department of Agriculture. The government has certain rights in the invention.--

Signed and Sealed this

Sixth Day of October, 1992

*Attest:*

DOUGLAS B. COMER

*Attesting Officer*  Acting Commissioner of Patents and Trademarks